US006086550A

United States Patent [19]

Richardson

[11] Patent Number: 6,086,550

[45] Date of Patent: Jul. 11, 2000

[54] APPARATUS FOR IMPARTING A ROCKING MOTION TO THE LEGS AND TORSO OF A USER

[76] Inventor: Ronald L. Richardson, 335 Lake Placid Estates, Seguin, Tex. 78155

[21] Appl. No.: 08/505,778

[22] Filed: Jul. 21, 1995

[51] Int. Cl.[7] .................. A61N 1/00

[52] U.S. Cl. .................. 601/26; 601/31; 601/35

[58] Field of Search .................. 601/35, 34, 24, 601/25, 4

[56] References Cited

U.S. PATENT DOCUMENTS 4,967,736 11/1990 Spitzer .................. 601/35

*Primary Examiner*—Max Hindenburg
*Assistant Examiner*—Pamela L. Wingood
*Attorney, Agent, or Firm*—Christopher L. Makay

[57] ABSTRACT

An apparatus for imparting a rocking motion to the legs and torso of a user includes a base, a leg rest removably mounted on the base to support the legs of the user, and a drive system positioned within the base for driving an upper portion of the base to impart a rocking motion to the user.

7 Claims, 2 Drawing Sheets

APPARATUS FOR IMPARTING A ROCKING MOTION TO THE LEGS AND TORSO OF A USER

BACKGROUND OF THE INVENTION

1. Field of the Invention

The present invention relates to therapeutic apparatus and, more particularly, but not by way of limitation, to an apparatus that imparts a variable speed rocking motion to the legs and torso of a user.

2. Description of the Related Art

A major concern in the medical field is the deleterious effects extended bed rest has on a person's body. When a person remains in bed for an extended period, breathing and digestion become difficult, heart functions decrease, blood circulation lessens, and muscle tissue and bones atrophy. Each of the above deleterious effects of extended bed rest weakens the body, and some cause potentially life threatening problems. For example, decreased heart functions and circulation may lead to blood clots and an increased risk of stroke. Additionally, a decrease in the ability to breathe causes fluid build-up in the lungs which leads to pneumonia.

In view of the potential seriousness of the above problems, devices that agitate a bed ridden person in an attempt to alleviate them have been developed. These devices typically consist of a bed that tilts from side to side to gently roll a person back and forth thereby imparting some movement to the body. Unfortunately, such beds are extremely expensive and, thus, typically found only in hospitals or nursing homes. A person subjected to bed rest at home normally cannot afford a specialized bed and, therefore, experiences bodily deterioration.

Accordingly, an inexpensive and portable apparatus that imparts a rocking motion to a person thereby alleviating the above-described problems would significantly improve the health of persons requiring bed rest at home.

SUMMARY OF THE INVENTION

In accordance with the present invention, an apparatus for imparting a rocking motion to the legs and torso of a user includes a base, a leg rest removably mounted on the base to support the legs of the user, and a drive system positioned within the base for driving an upper portion of the base to impart a rocking motion to the user.

The base includes a first support member, a second support member, a bottom spanning the first support member, and a pair of rocker arms connecting the second support member to the bottom. Each rocker arm includes a first bearing mounted to the bottom, a second bearing mounted to the second support member, and a shaft connecting the first bearing to the second bearing. The first and second bearings pivot to permit the drive system to drive the second support member.

The drive system includes a motor and a motor speed controller. A transmission having first and second drive shafts is coupled to the motor. First and second cams are coupled to the first and second drive shafts, respectively. First and second brackets connect between the first and second cams and the second support member wherein the first and second cams drive their respective brackets via bearings to move the second support member along an elliptical path that imparts a rocking motion to the user.

It is therefore an object of the present invention to provide an apparatus that imparts a rocking motion to the legs and torso of a user to prevent body deterioration during bed rest.

It is another object of the present invention to make the apparatus portable to allow for home use.

Still other objects, features, and advantages of the present invention will become evident to those of ordinary skill in the art in light of the following.

DETAILED DESCRIPTION OF THE PREFERRED EMBODIMENT

Figure 1:
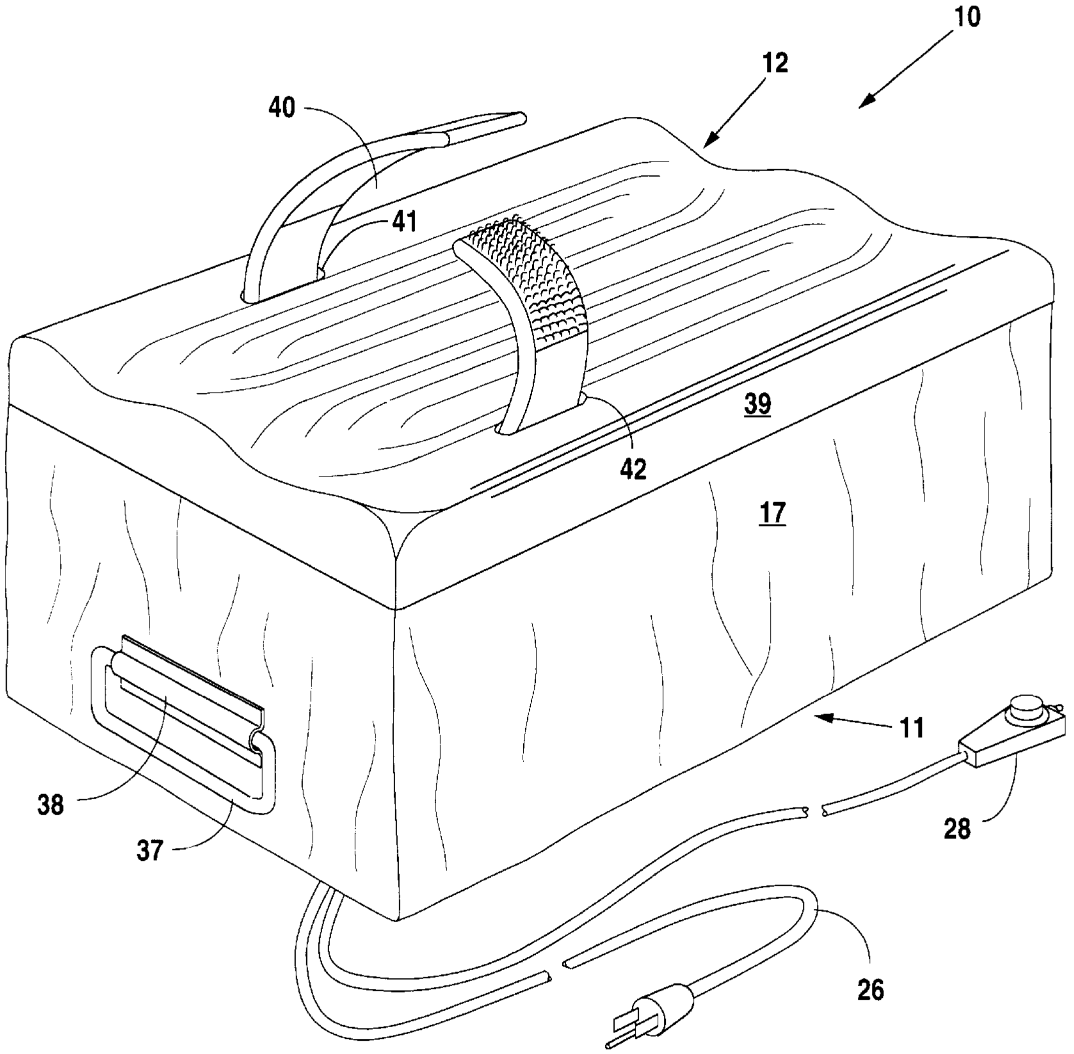
FIG. 1 is a perspective view illustrating the apparatus for imparting a variable speed rocking motion to the legs and torso of a user.
Figure 2:
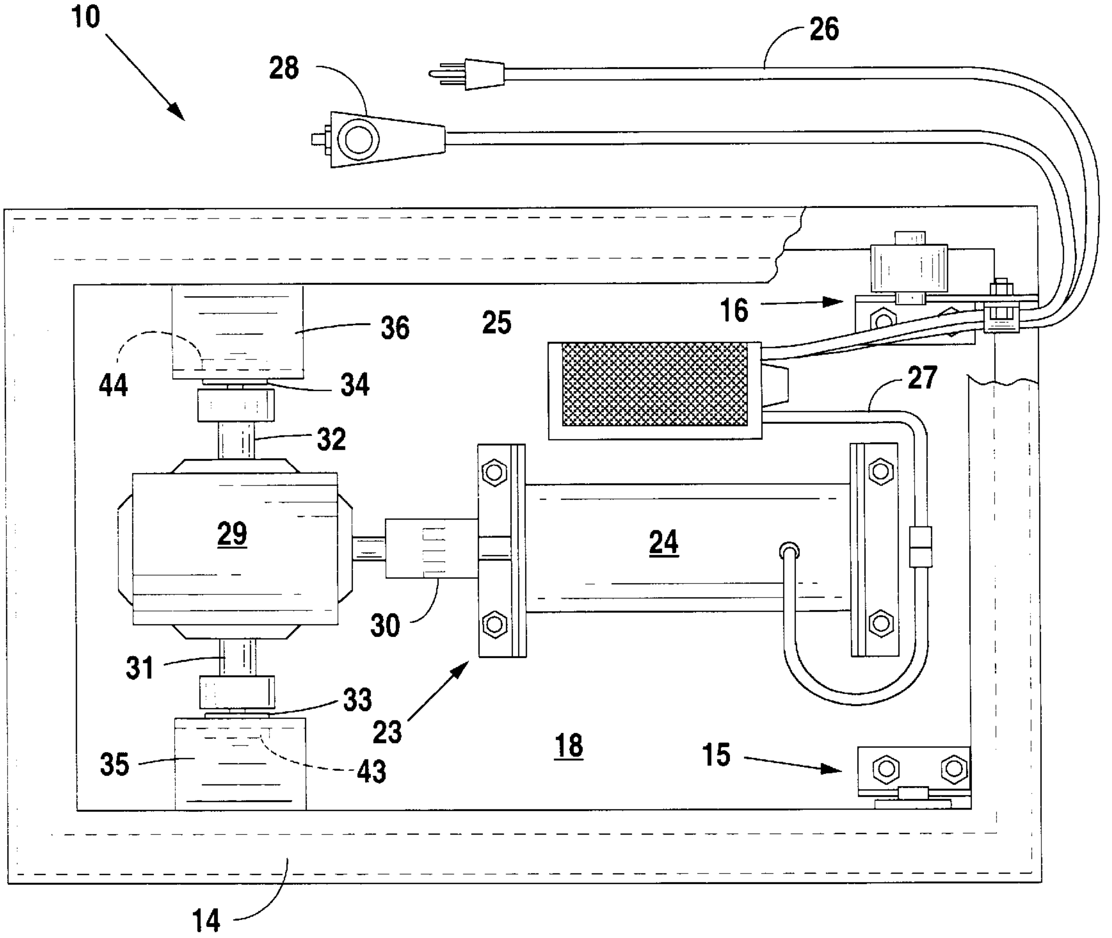
FIG. 2 is a top plan view illustrating the apparatus for imparting a variable speed rocking motion to the legs and torso of a user.
Figure 3:
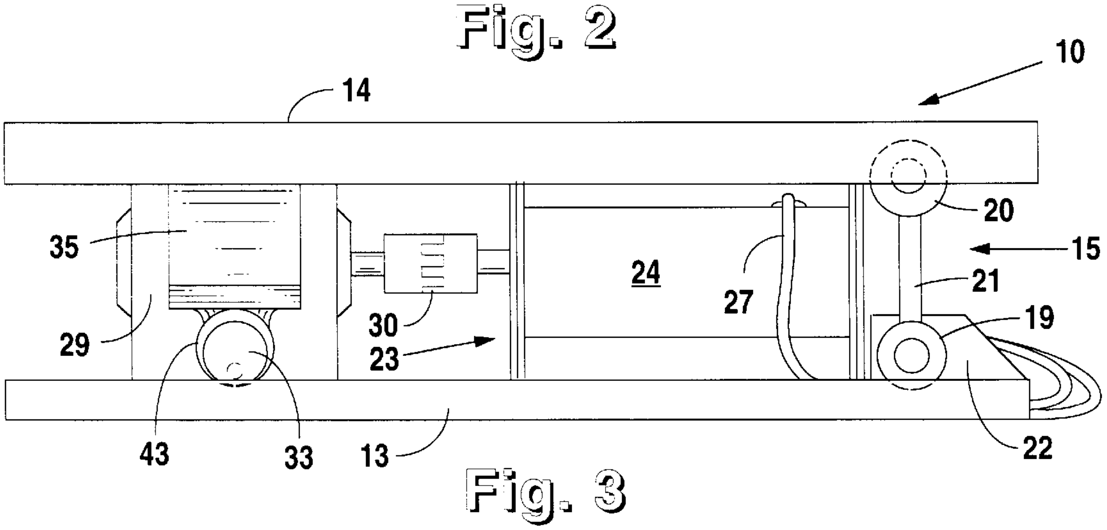
FIG. 3 is a side plan view illustrating the apparatus for imparting a variable speed rocking motion to the legs and torso of a user.

As illustrated in FIGS. 1–3, apparatus 10 for imparting a variable speed rocking motion to the legs and torso of a user includes base 11 and leg rest 12 removably mounted thereon. Base 11 includes support members 13 and 14 and bottom 18 that spans support member 13 and is attached thereto using any suitable means such as screws or nuts and bolts. Rocker arms 15 and 16 mount at one end to bottom 18 and at an opposite end to support member 14 to space apart support members 13 and 14. In this preferred embodiment, support members 13 and 14 are rectangular in shape and constructed from any suitable material such as metal to provide a frame for covering 17. Covering 17 fits loosely around support members 13 and 14 to permit the motion of support member 14. In this preferred embodiment, covering 17 attaches to support members 13 and 14 using any suitable means such an adhesive and may be any suitable material such as vinyl.

Rocker arm 15 includes bearings 19 and 20 interconnected by shaft 21. Bracket 22 mounts onto bottom 18 using any suitable means such as nuts and bolts to provide a connection point for bearing 19. Bearing 19 mounts onto bracket 22, while bearing 20 mounts directly onto support member 14. Bearings 19 and 20 mount to bracket 22 and support member 14, respectively, using any suitable means such as welding. Shaft 21 includes pivot pins that reside within bearings 19 and 20 to permit movement of support member 14 in an elliptical path (i.e., forward, upward, backward, and downward or vice versa). Rocker arm 16 is identical to rocker arm 15 and, therefore, has not been described.

Base 11 includes handle 37 to provide easy portability of apparatus 10. Bracket 38 of handle 37 mounts over cover 17 onto support member 13 using any suitable means such as nuts and bolts.

Drive system 23 mounts within base 11 to drive support member 14 in an elliptical path. As support member 14 travels along its elliptical path, it moves base 11 such that base 11 imparts a rocking motion to a user's legs and torso. Drive system 23 includes motor 24 which mounts to bottom 18 using any suitable means such as brackets and nuts and bolts. In this preferred embodiment, motor 24 is an ⅛ horsepower DC motor.

Drive system 23 further includes motor controller 25 that provides motor 24 with DC power and permits user regulation of its speed. In this preferred embodiment, motor controller 25 is a Serial No. 125d speed control device manufactured by Dart Control, Inc. Motor controller 25 connects to outlet cord 26 to supply DC power to motor 24 via cord 27. Outlet cord 26 plugs into any standard 115/120 VAC outlet to allow the application of power to drive system 23. Additionally, motor controller 25 connects to control switch 28 that permits user control of motor controller 25 and, thus, the speed control of motor 24. In this preferred embodiment, control switch 28 may be any suitable device that regulates the delivery of power such as a variable resistor.

Drive system 23 still further includes transmission 29 that connects to the drive shaft of motor 24 via coupling member 32. Transmission 29 imparts the rotational motion of motor 24 to support member 14 via its drive shafts 31 and 32, cams 33 and 34, and brackets 35 and 36. In this preferred embodiment, transmission 29 is a Model No. 1034 IPTS power transmission manufactured by Indiana Power Transmission, Inc. As motor 24 rotatably drives its drive shaft, transmission 29 transfers that motion to its drive shafts 31 and 32 which rotate accordingly. Drive shafts 31 and 32 connect off center from their respective cams 33 and 34 using any suitable means such as welding. That off center connection causes cams 33 and 34 to define an elliptical path as shafts 31 and 32 rotate them. Consequently, brackets 35 and 36, which connect to their respective cams 33 and 34 via bearings 43 and 44, respectively, and support member 14 using any suitable means such as welding, also travel along an elliptical path as they move support member 14.

Leg rest 12 includes a frame (not shown) having a bottom (not shown) that supports any suitable type padding. Cover 39 resides about the padding and attaches to the bottom using any suitable means such as staples. In this preferred embodiment, cover 39 may be any suitable material such as vinyl. Leg rest 12 includes strap 40 that mounts through openings 41 and 42 in cover 39. The ends of strap 40 are secured together any suitable means such as velcro to hold a user's legs securely on leg rest 12.

Figure 4:
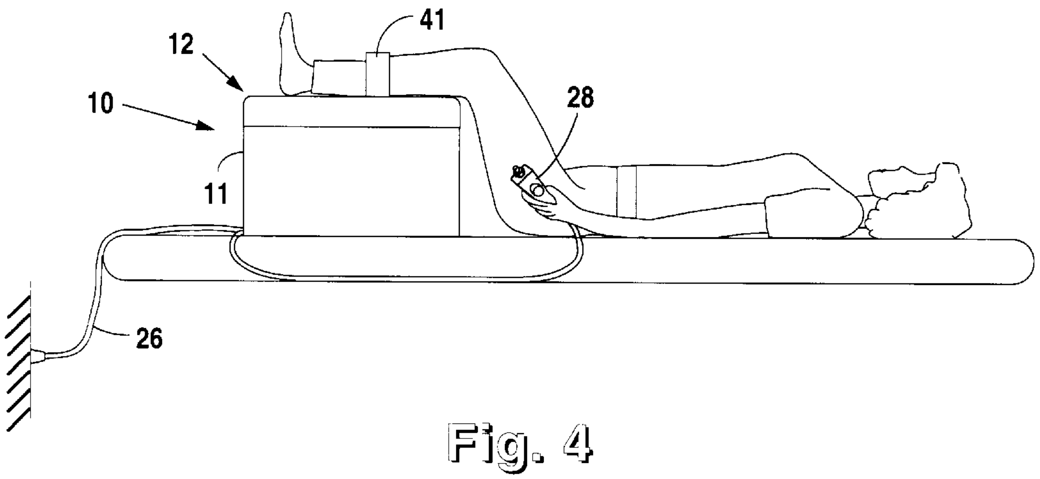
FIG. 4 is a side plan view illustrating the operation of the apparatus for imparting a variable speed rocking motion to the legs and torso of a user.

In operation as illustrated in FIG. 4, a user places apparatus 10 on any suitable flat surface and plugs cord 26 into any standard 115/120 VAC outlet. The user then lays down and places his/her feet on leg rest 12 and secures them with strap 40. The user then turns on motor 24 and selects its speed via control switch 28. With power applied, motor 24 drives transmission 29 which in turn drives cams 33 and 34 and thus brackets 35 and 36 via bearings in an elliptical path. As a result, support member 14 and thus the upper portion of base 11 initially travel towards the user due to the pivoting of rocker arms 15 and 16 along their lower bearings. As support member 14 travels towards the user, it also travels upward due to the pivoting of rocker arms 15 and 16 along their upper bearing. Cams 33 and 34 and rocker arms 15 and 16 are synchronized such that, when rocker arms 15 and 16 reach the extent of their forward and upward pivoting, cams 33 and 34 drive their respective brackets 35 and 36 to move support member 14 and thus base 11 backwards and down. Support member 14 travels backwards and down until it again reaches a level position whereupon drive system 23 again drives it along its elliptical path.

Accordingly, the upper portion of base 11 and leg support 12 travel in an elliptical path that imparts a rocking motion to the legs and torso of the user. That rocking motion works the body such that the muscles are exercised thereby increasing both circulation and heart rate. Specifically, the user's legs move elliptically which stimulates the muscles, while his/her pelvic region and lower back are stretched. Furthermore, the rocking motion enhances breathing because it alternately compresses and expands the user's diaphragm. That is, during the forward and upper motion of support member 14, the user's legs are forced over their abdomen which compresses the diaphragm. On the rearward and downward motion of support member 14, the user's legs travel away from his/her abdomen which causes the diaphragm to expand to allow a greater intake of oxygen into the lungs. Apparatus 10, therefore, provides a portable device that prevents bed ridden persons from experiencing bodily deterioration. Although apparatus 10 has been described as a portable device, those of ordinary skill in the art will readily recognize that it could be incorporated into a permanent structure such as a bed.

Although the present invention has been described in terms of the foregoing embodiment, such description has been for exemplary purposes only and, as will be apparent to those of ordinary skill in the art, many alternatives, equivalents, and variations of varying degrees will fall within the scope of the present invention. That scope, accordingly, is not to be limited in any respect by the forgoing description, rather, it is defined only by the claims that follow.

I claim:

1. An apparatus for imparting a rocking motion to the legs and torso of a user, comprising:

a base having an upper portion;

a leg rest removably mounted on said upper portion of said base to support the legs of the user; and a drive system positioned within said base for driving the upper portion of said base along an elliptical path that imparts an enhanced rocking motion to the user.

2. The apparatus according to claim 1 wherein said base comprises:

a first support member;

a second support member;

a bottom spanning said first support member; and a pair of rocker arms connecting said second support member to said bottom wherein said rocker arms pivot to permit said drive system to drive said second support member.

3. The apparatus according to claim 2 wherein each of said rocker arms comprises:

a first bearing mounted to said bottom;

a second bearing mounted to said second support member; and a shaft connecting said first bearing to said second bearing.

4. The apparatus according to claim 2 wherein said drive system comprises:

a motor;

means for controlling motor speed;

a transmission coupled to said motor, said transmission including first and second drive shafts;

a first cam connected to said first drive shaft;

a second cam connected to said second drive shaft;

a first bracket connected between said first cam via a first bearing and said second support member wherein said first cam drives said first bracket to move said second support member along an elliptical path that imparts a rocking motion to the user; and a second bracket connected between said second cam via a second bearing and said second support member wherein said second cam drives said second bracket to move said second support member along an elliptical path that imparts a rocking motion to the user.

5. The apparatus according to claim 4 wherein said means for controlling motor speed comprises:

a control switch for translating user input into a control signal; and a motor controller that receives said control signal and utilizes said control signal to regulate motor speed.

6. The apparatus according to claim 1 wherein said base includes a handle to provide portability.

7. The apparatus according to claim 1 wherein said leg rest includes a strap to secure the legs of the user to the leg rest.

* * * * *